（12) United States Patent
Ridley et al.

(10) Patent No.: US 11,304,707 B2
(45) Date of Patent: Apr. 19, 2022

(54) ROTARY MILL

(71) Applicants: Biomet UK Healthcare Limited, Bridgend (GB); David Wycliffe Murray; Christopher Dodd; John Joseph O'Connor

(72) Inventors: Duncan Andrew Ridley, Bristol (GB); Mona Alinejad, London (GB); Russell Lloyd, Swindon (GB); David Wycliffe Murray, Oxford (GB); Christopher Dodd, Oxford (GB); John Joseph O'Connor, Oxford (GB)

(73) Assignee: Biomet UK Healthcare Limited, Bridgend (GB)

( * ) Notice: Subject to any disclaimer, the term of this patent is extended or adjusted under 35 U.S.C. 154(b) by 328 days.

(21) Appl. No.: 16/533,427

(22) Filed: Aug. 6, 2019

(65) Prior Publication Data

US 2019/0357921 A1 Nov. 28, 2019

Related U.S. Application Data

(63) Continuation of application No. 15/027,601, filed as application No. PCT/GB2014/052959 on Sep. 30, 2014, now abandoned.

(30) Foreign Application Priority Data

Oct. 7, 2013 (GB) ...................................... 1317656

(51) Int. Cl.
*A61B 17/00* (2006.01)
*A61B 17/16* (2006.01)
*A61B 17/17* (2006.01)

(52) U.S. Cl.
CPC .......... *A61B 17/16* (2013.01); *A61B 17/1675* (2013.01); *A61B 17/17* (2013.01); *A61B 17/1764* (2013.01); *A61B 2017/1602* (2013.01)

(58) Field of Classification Search
CPC combination set(s) only.
See application file for complete search history.

(56) References Cited

U.S. PATENT DOCUMENTS

| 4,193,721 A | 3/1980 | Hougen |
| 5,002,547 A | 3/1991 | Poggie et al. |

(Continued)

FOREIGN PATENT DOCUMENTS

| CA | 2825675 | 10/2016 |
| EP | 1374804 | 1/2004 |

(Continued)

OTHER PUBLICATIONS

U.S. Appl. No. 13/981,949 U.S. Pat. No. 9,770,249, filed Mar. 3, 2014, Rotary Mill.

(Continued)

*Primary Examiner* — Sameh R Boles
(74) *Attorney, Agent, or Firm* — Schwegman Lundberg & Woessner, P.A.

(57) ABSTRACT

A rotary mill comprising a body portion having a milling surface for milling a first bone, a guide portion having a guide body, and inter-engageable guide formations formed on the body portion and guide portion, the guide body having a projection which is adapted to hold a second bone away from the rotary mill during the milling operation.

18 Claims, 6 Drawing Sheets

(56) References Cited

U.S. PATENT DOCUMENTS

| | | | |
|---|---|---|---|
| 5,171,313 | A | 12/1992 | Salyer |
| 5,314,482 | A | 5/1994 | Goodfellow et al. |
| 5,336,226 | A | 8/1994 | Mcdaniel et al. |
| 6,322,564 | B1 | 11/2001 | Surma |
| 6,827,741 | B2 | 12/2004 | Reeder |
| 7,306,607 | B2 | 12/2007 | Metzger |
| 7,527,631 | B2 | 5/2009 | Maroney et al. |
| 7,695,520 | B2 | 4/2010 | Metzger et al. |
| 9,770,249 | B2 | 9/2017 | Goodfellow |
| 10,568,645 | B2 | 2/2020 | Goodfellow et al. |
| 2006/0015111 | A1 | 1/2006 | Fenton |
| 2006/0089621 | A1 | 4/2006 | Fard |
| 2007/0203500 | A1 | 8/2007 | Gordon et al. |
| 2007/0276394 | A1 | 11/2007 | Johnson et al. |
| 2007/0282451 | A1 | 12/2007 | Metzger et al. |
| 2010/0042103 | A1 | 2/2010 | Rasmussen |
| 2010/0198224 | A1 | 8/2010 | Metzger |
| 2010/0222781 | A1 | 9/2010 | Collazo et al. |
| 2011/0106093 | A1 | 5/2011 | Romano et al. |
| 2015/0066034 | A1 | 3/2015 | Goodfellow et al. |
| 2016/0235415 | A1 | 8/2016 | Ridley et al. |
| 2018/0078264 | A1 | 3/2018 | Goodfellow et al. |
| 2019/0008529 | A1 | 1/2019 | Goodfellow et al. |

FOREIGN PATENT DOCUMENTS

| | | | |
|---|---|---|---|
| EP | 1864617 | | 12/2007 |
| EP | 2181672 | | 5/2010 |
| EP | 2667797 | | 12/2013 |
| EP | 2774555 | | 9/2014 |
| EP | 3054863 | | 8/2016 |
| GB | 2487562 | | 8/2012 |
| GB | 2518891 | | 4/2015 |
| GB | 2487562 | | 4/2017 |
| JP | 61127913 | | 6/1986 |
| JP | 01250250 | | 10/1989 |
| JP | 01308555 | | 12/1989 |
| JP | 08502681 | | 3/1996 |
| JP | 2005046625 | | 2/2005 |
| JP | 5991549 | | 9/2016 |
| WO | WO-2006001010 | A1 * | 1/2006 ......... A61B 17/1778 |
| WO | 2012101441 | | 8/2012 |
| WO | 2015052490 | | 4/2015 |

OTHER PUBLICATIONS

U.S. Appl. No. 15/713,816, filed Sep. 25, 2017, Rotary Mill.
U.S. Appl. No. 16/035,014, filed Jul. 13, 2018, Rotary Mill.
U.S. Appl. No. 15/027,601, filed Apr. 6, 2016, Rotary Mill.
"U.S. Appl. No. 13/981,949, Preliminary Amendment filed Jul. 26, 2013", 9 pgs.
"Canadian Application Serial No. 2,825,675, Office Action dated Jul. 20, 2015", 5 pgs.
"Canadian Application Serial No. 2,887,742, Office Action dated Jul. 15, 2015", 4 pgs.
"International Application Serial No. PCT GB2012 050159, International Search Report dated Apr. 3, 2012", 5 pgs.
"International Application Serial No. PCT GB2012 050159, Written Opinion dated Apr. 3, 2012", 8 pgs.
"International Application Serial No. PCT GB2012 050159, International Preliminary Report on Patentability dated Aug. 8, 2013", 10 pgs.
"United Kingdom Application Serial No. 1101377.8, Search Report dated Apr. 14, 2011", 1 pg.
"Japanese Application Serial No. 2013-550950, Office Action dated Dec. 7, 2015", w English Translation, 6 pgs.
"Canadian Application Serial No. 2,887,742, Response filed Jan. 15, 2016 to Office Action dated Jul. 15, 2015", 4 pgs.
"Japanese Application Serial No. 2013-550950, Response filed Mar. 7, 2016 to Office Action dated Dec. 7, 2015", w English Claims, 6 pgs.

"International Application Serial No. PCT GB2014 052959, International Search Report dated Dec. 18, 2014", 6 pgs.
"International Application Serial No. PCT GB2014 052959, Written Opinion dated Dec. 18, 2014", 7 pgs.
"International Application Serial No. PCT GB2014 052959, International Preliminary Report on Patentability dated Apr. 21, 2016", 9 pgs.
"U.S. Appl. No. 13/981,949, Restriction Requirement dated May 4, 2016", 9 pgs.
"Canadian Application Serial No. 2,887,742, Office Action dated May 24, 2016", 3 pgs.
"U.S. Appl. No. 13/981,949, Response filed Jun. 7, 2016 to Restriction Requirement dated May 4, 2016", 9 pgs.
"U.S. Appl. No. 13/981,949, Non Final Office Action dated Sep. 7, 2016", 13 pgs.
"United Kingdom Application Serial No. 1101377.8, Office Action dated Sep. 27, 2016", 3 pgs.
"Canadian Application Serial No. 2,887,742, Response filed Oct. 25, 2016 to Office Action dated May 24, 2016", 3 pgs.
"U.S. Appl. No. 13/98,949, Response filed Dec. 2, 2016 to Non Final Office Action dated Sep. 7, 2016", 16 pgs.
"United Kingdom Application Serial No. 1101377.8, Response filed Nov. 28, 2016 to Office Action dated Sep. 27, 2016", 14 pgs.
"United Kingdom Application Serial No. 1101377.8, Office Action dated Dec. 20, 2016", 2 pgs.
"European Application Serial No. 14784347.8, Response filed Dec. 29, 2016 to Communication pursuant to Rules 161(1) and 162 EPC dated Jun. 21, 2016", 9 pgs.
"United Kingdom Application Serial No. 1101377.8, Response filed Feb. 9, 2017 to Office Action dated Dec. 26, 2016", 7 pgs.
"United Kingdom Application Serial No. 1101377.8, Office Action dated Feb. 16, 2017", 2 pgs.
"U.S. Appl. No. 13/981,949, Final Office Action dated Mar. 6, 2017", 8 pgs.
"U.S. Appl. No. 13/981,949, Response filed Mar. 27, 2017 to Final Office Aciton dated Mar. 6, 2017", 10 pgs.
"U.S. Appl. No. 13/981,949, Notice of Allowance dated Apr. 4, 2017", 5 pgs.
"United Kingdom Application Serial No. 1101377.8, Notice of Decision to Grant dated Mar. 28, 2017", 2 pgs.
"Canadian Application Serial No. 2,887,742, Notice of Allowance dated Jan. 26, 2017", 1 pg.
"U.S. Appl. No. 13/981,949, Notice of Allowance dated May 24, 2017", 7 pgs.
"U.S. Appl. No. 15/713,816, Preliminary Amendment filed Dec. 7, 2017", 6 pgs.
"U.S. Appl. No. 15/713,816, Notice of Allowance dated Apr. 13, 2018", 12 pgs.
"European Application Serial No. 14784347.8, Communication Pursuant to Article 94(3) EPC dated Jun. 4, 2018", 5 pgs.
"U.S. Appl. No. 16/035,014, Preliminary Amendment Filed Sep. 28, 2018", 6 pgs.
"European Application Serial No. 14784347.8, Response filed Oct. 30, 2018 to Communication Pursuant to Article 94(3) EPC dated Jun. 4, 2018", 10 pgs.
"U.S. Appl. No. 15/027,601, Restriction Requirement dated Dec. 18, 2018", 7 pgs.
"U.S. Appl. No. 15/027,601, Response filed Feb. 18, 2019 to Restriction Requirement dated Dec. 18, 2018", 7 pgs.
"U.S. Appl. No. 15/027,601, Non Final Office Action dated May 6, 2019", 7 pgs.
"United Kingdom Application Serial No. 1317656.5, Subsequent Examination Report dated Aug. 19, 2019", 2 pgs.
"U.S. Appl. No. 16/035,014, Notice of Allowance dated Oct. 25, 2019", 9 pgs.
"European Application Serial No. 14784347.8, Communication Pursuant to Article 94(3) EPC dated Sep. 22, 2021", 6 pgs.
"United Kingdom Application Serial No. 1317656.5, Intent to Grant Under Section 18(4) dated Jan. 3, 2020", 2 pgs.
"United Kingdom Application Serial No. 1317656.5, Response filed Oct. 21, 2019 Subsequent Examination Report dated Aug. 19, 2019", 6 pgs.

(56) References Cited

OTHER PUBLICATIONS

"United Kingdom Application Serial No. 1317656.5, Response filed Dec. 18, 2019 to Subsequent Examination Report dated Nov. 20, 2019", 7 pgs.
"United Kingdom Application Serial No. 1317656.5, Subsequent Examination Report dated Nov. 20, 2019", 1 pg.
"European Application Serial No. 14784347.8, Response filed Feb. 2, 2022 to Communication Pursuant to Article 94(3) EPC dated Sep. 22, 2021", 14 pages.

* cited by examiner

ROTARY MILL

CLAIM OF PRIORITY

This application is a continuation of U.S. application Ser. No. 15/027,601, filed Apr. 6, 2016, which is a U.S. National Stage Filing under 35 U.S.C. 371 from International Application No. PCT/GB2014/052959, filed on 30 Sep. 2014, and published as WO 2015/052490 A1 on 16 Apr. 2015, which claims the benefit to United Kingdom Application No. 1317656.5, filed on 7 Oct. 2013, the benefit of priority of each of which is claimed hereby, and each of which are incorporated by reference herein in its entirety.

The present invention relates to rotary mills and similar rotary cutting devices and particularly but not exclusively relates to rotary mills for use in preparing a bone for total or partial joint replacement surgery.

BACKGROUND

It is known to replace all or part of a knee joint, in which the joint surfaces have deteriorated, for example as a result of osteoarthritis. Such deterioration usually starts in only one of the tibeo-femoral compartments and may spread to the other at a later stage. Replacement of only one compartment of the joint can therefore be sufficient to provide prolonged relief from symptoms. Damaged bearing surfaces are replaced by a unicompartmental prosthesis which comprises a femoral implant and a tibial implant (usually metallic), which interface through a (polyethylene) bearing component disposed between the two implants.

A unicompartmental or partial knee replacement (PKR) helps to conserve undamaged bone and restores more natural movement to the joint. Also, owing to the small site of the prosthesis, the surgery may be less invasive than a total knee replacement (TKR). However, the design requirements for partial knee replacement prostheses are more demanding than those for total knee replacement prostheses. Unlike in a total knee replacement, where one or more ligaments can be discarded and the mechanics of the knee can be simplified, in a unicompartmental knee replacement, all the ligaments in the joint must be retained and restored to their natural tensions and the bearing component must be completely unconstrained.

Figure 1:
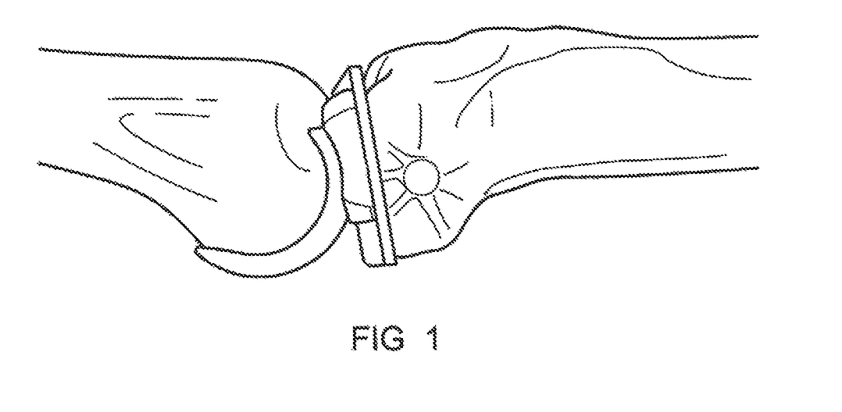
FIG. 1 shows impingement of a meniscal earing on anterior femoral bone.

During articulation of the knee, and particularly when the joint is at full extension, the bearing component can impinge on femoral condylar bone tissue superior to the femoral implant, as illustrated in FIG. 1. Such impingement of the polyethylene bearing component onto the bone can lead to post operative pain, damage to the bearing, increased wear and eventual failure. It is therefore essential to remove a sufficient amount of anterior bone on the femoral condyle during the implantation procedure to prevent such impingement from occurring.

The appropriate amount of bone is removed from the femoral condyle using a rotary mill. This procedure is carried out with the leg flexed, so that the rotary mill is clear of the tibia. If the leg is insufficiently flexed or the anatomy of the patient is such that the tibia projects more than is normal, it is possible that the rotary could contact tibia, during milling of the femoral condyle, thereby causing undesirable milling of the surface of the tibia.

SUMMARY OF INVENTION

According to the present invention there is provided a rotary mill comprising a body portion having a milling surface for milling a first bone, a guide portion having a guide body, and inter-engageable guide formations formed on the body portion and guide portion, the guide body having a projection which is adapted to hold a second bone away from the rotary mill during the milling operation.

The inter-engageable guide formations may comprise a central bore extending along the rotary axis of the body portion and a guide peg extending from the guide body, the guide peg being operable to be received in the central bore of the body portion.

The projection may be integrally formed with the guide body.

The projection may comprise an arm which is shaped to receive the milling surface without impingement over its full range of movement relative to the guide body. The arm may be shaped to receive the milling surface closely over its full range of movement relative to the guide body.

The arm may be provided with a recess on a first side which is adapted to accommodate milling surface without impingement. An opposite side of the arm may be polished chamfered or otherwise shaped such that it does not damage the second bone.

The guide body may include at least one nodule, protruding from a surface of the guide body and operable to abut a corresponding abutment surface on the body portion. The nodules may thus act as depth stops to ensure a precise amount of bone is removed and avoid excessive bone removal.

The guide peg may comprise an abutment surface operable to abut a corresponding abutment surface in the central bore of the body portion. The guide peg may thus not only act to guide the angle at which the body portion mills bone surface but may also act as a depth stop to limit bone removal.

The abutment surface may comprise a distal surface of the peg or the abutment surface may comprise an outwardly projecting annular shoulder.

The corresponding abutment surface of the central bore may comprise a base of the bore or may comprise an inwardly projecting annular shoulder.

The guide body may be operable to be connected to additional surgical tools, thus facilitating and providing reference for additional bone removal steps.

The guide body may have substantially the form of a trial prosthesis component and may in fact comprise a trial prosthesis component. The guide body may comprise a trial femoral prosthesis component which may be a trial unicondylar femoral prosthesis component.

The projection may extend from the guide body in a direction substantially parallel to a longitudinal axis of the guide peg.

The guide body may be operable to be connected to a posterior osteophyte guide.

The rotary mill may further comprise additional guide portions, each guide portion being of a different size so as to match differently sized prosthesis components that are employed for patents of differing sizes.

BRIEF DESCRIPTION OF DRAWINGS

For a better understanding of the present invention, and to show more clearly how it may be carried into effect, reference will now be made, by way of example, to the following drawings, in which.

DETAILED DESCRIPTION

Figure 10:
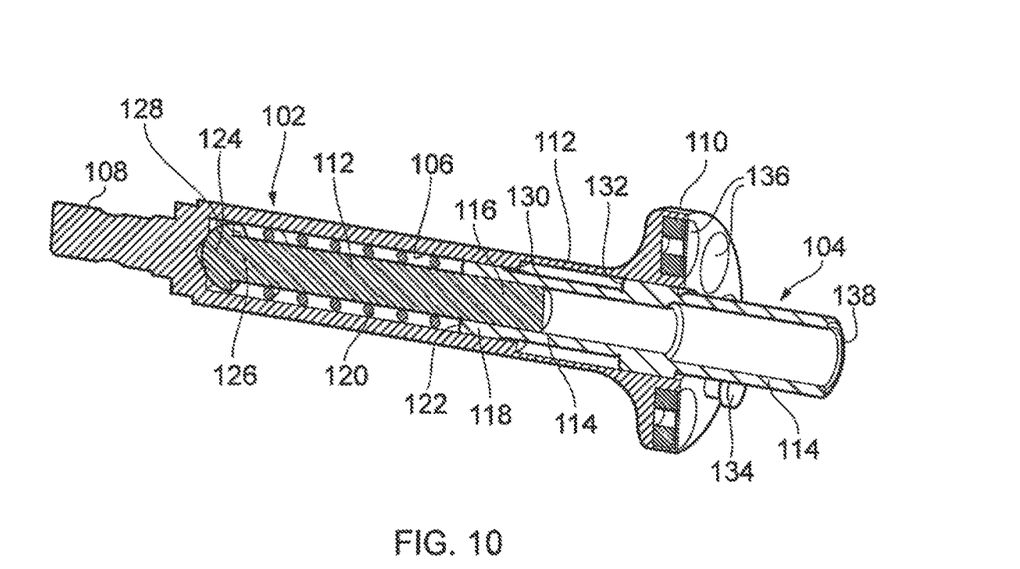
FIG. 10 is a sectional view of a rotary cutting tool.
Figure 11:
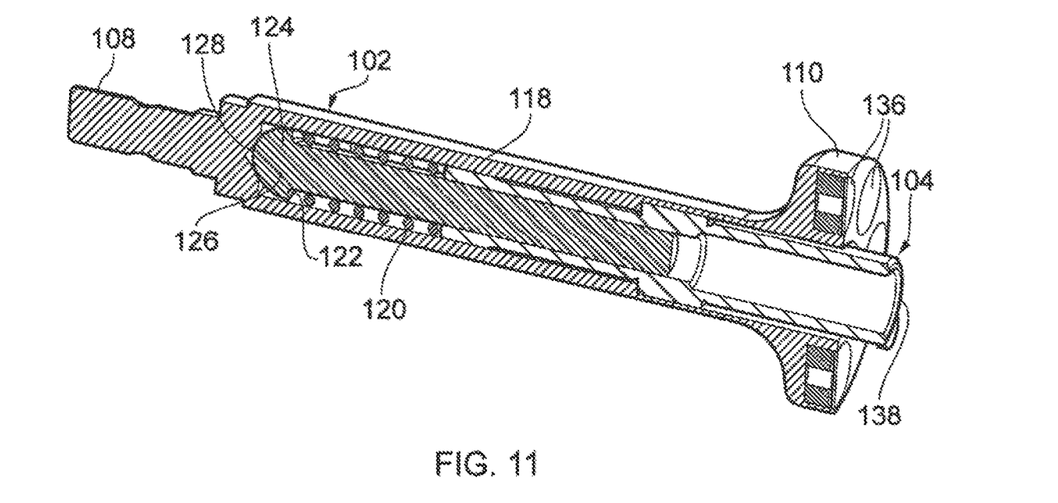
FIG. 11 is a sectional view of the tool of FIG. 10 in a compressed condition.
Figure 12:
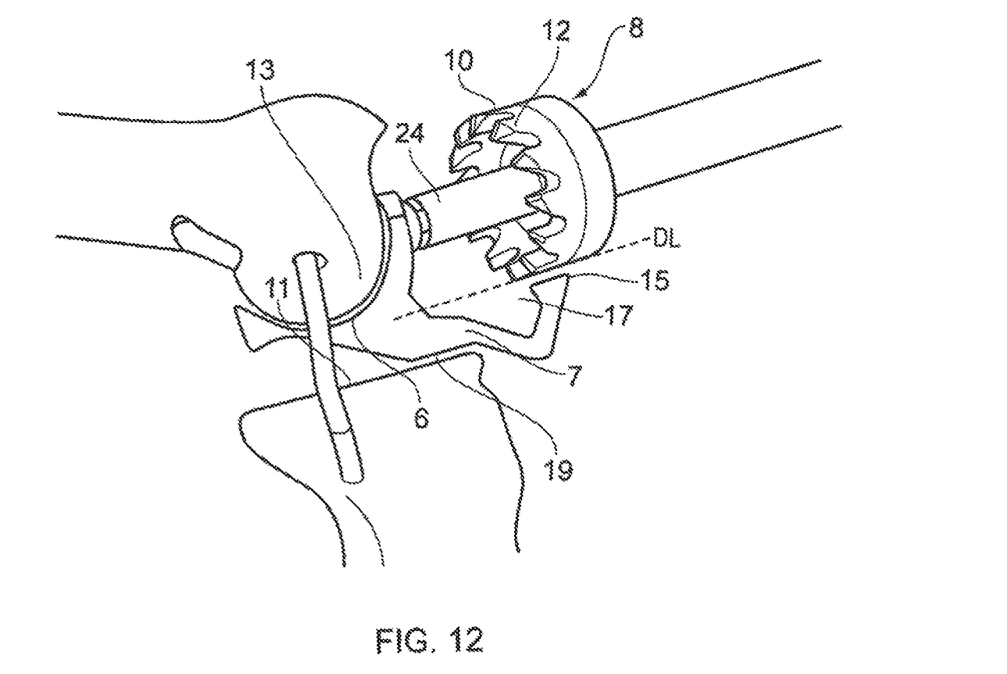
FIG. 12 shows a modified guide portion having a cutting guard which protects the tibia during milling.

FIGS. 1 to 11 illustrate the use of a rotary mill having a standard guide portion, whereas FIG. 12 illustrates a modified guide portion having a cutting guard in accordance with the present invention.

Figure 2:
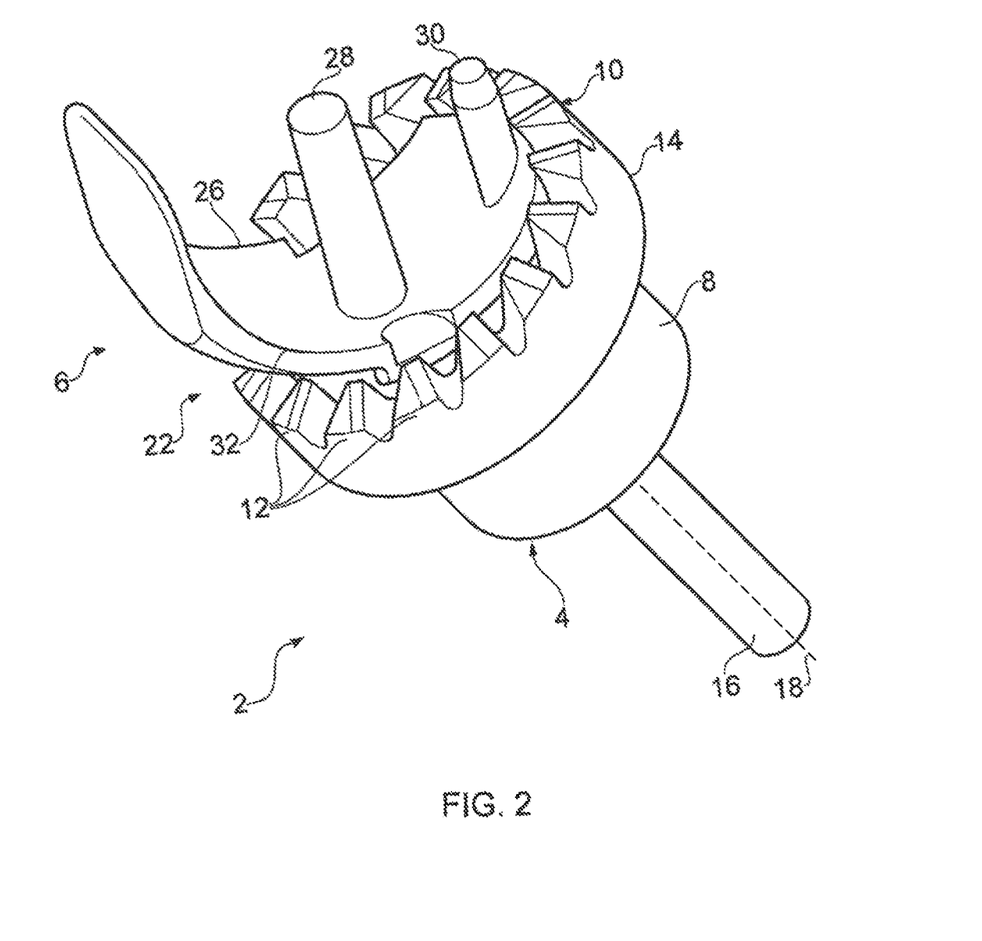
FIG. 2 is a perspective view of a rotary mill.

With reference to FIG. 2, a rotary mill 2 comprises a body portion 4 and a guide portion 6. The body portion 4 comprises a rotary body 8 that terminates at one end in an annular milling surface 10. The milling surface comprises a series of milling teeth 12 that extend from the surface 10. In the illustrated embodiment, the milling surface 10 is formed on an annular shoulder 14 that protrudes outwardly from the rotary body 8. An abutment surface 15 extends radially inwardly of the projecting milling surface 10. At a second end of the rotary body 8 an integral shank 16 extends along an axis of rotation 18 of the rotary body. The shank 16 is suitable for attachment to the chuck of a surgical drill (not shown). A bore 20 extends through the rotary body 8 along the axis of rotation 18 of the rotary body 8. With reference to FIG. 12, the guide portion 6 is provided with a guard projection 7 in the form of an arm which extends to one side of the annular milling surface 10 between the rotary body 8 and a proximal tibial surface 11. The guard projection 7 ensures that the guide portion 6 can only be fitted when the leg of a patent is sufficiently flexed and prevents tibial impingement as illustrated in FIG. 4, where the annular milling surface 10 contacts the tibia as it travels along the fine DL during milling of the femur.

Figure 3:
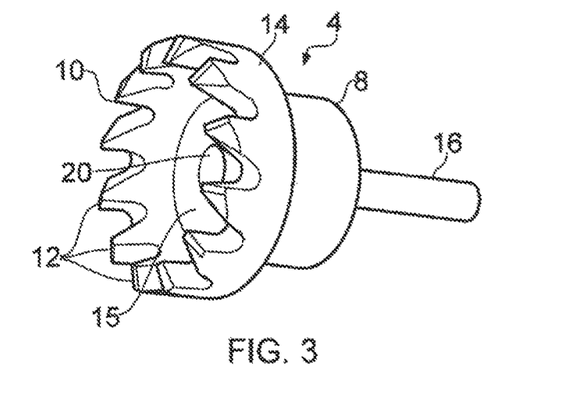
FIG. 3 is a perspective view of a body portion of a rotary mill.
Figure 4:
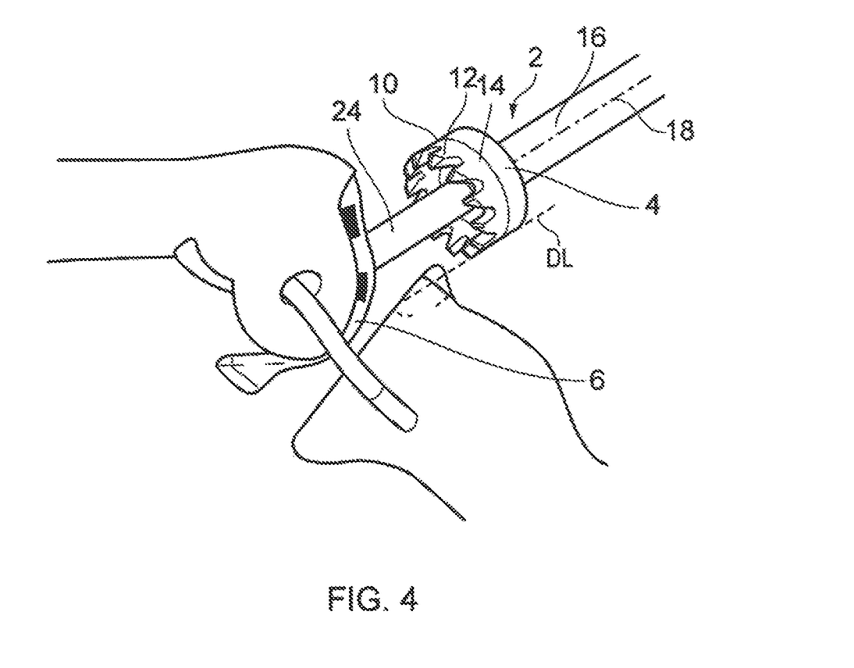
FIG. 4 shows a guide portion of a rotary mill in position on a femur.
Figure 6:
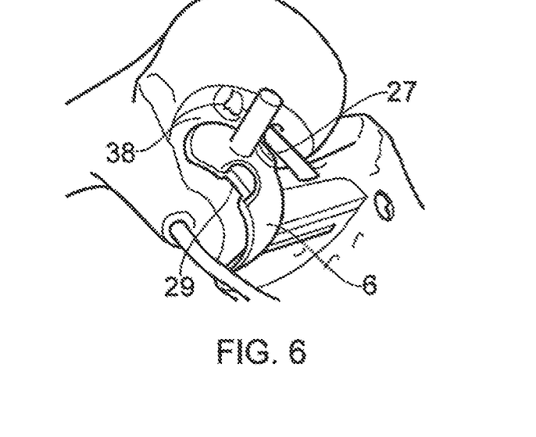
FIG. 6 illustrates bone removal by a rotary mill.

With reference to FIGS. 2 to 4, the guide portion 6 comprises a guide body 22 and a guide peg 24. The guide body 22 comprises a trail unicondylar femoral prosthesis component. The guide body thus comprises a curved condylar plate 26 and two attachment pegs 28, 30. The attachment pegs 28, 30 protrude from a bone contacting surface 32 of the condylar plate 26 at locations and angles precisely matching those of a similarly sized prosthesis component. The guide body can thus be attached to a prepared femoral condylar surface in the same manner and using the same drilled peg holes as for a prosthesis component. In this manner, the attachment pegs 28, 30 serve to align the guide body with the eventual location of the femoral prosthesis, referencing off the pre prepared drilled femoral peg holes. The guide peg 24 is a cylindrical peg that protrudes from an opposite, outer surface 34 of the condylar plate 26. The guide peg 24 extends from an anterior portion of the condylar plate 26 along an axis that is substantially normal to the adjacent condylar plate surface 34. The guide peg 24 projects at an angle of between 25 and 40 degrees to the axis of the attachment pegs. The precise angle is selected according to the size of the guide portion and associated anatomy, as discussed in further detail below. The guide peg dimensioned to be slidably and rotatably received within the central bore 20 of the rotary body 8. With reference also to FIG. 6, two nodules 27, 29 protrude from the outer surface 34 of the condylar plate 26. The nodules 27, 29 are formed on opposite sides of the anterior portion of the condylar plate 26, in the region of the guide peg 24.

The rotary mill 2 is used to remove anterior bone on the femoral condyle prior to implantation of a unicondylar femoral prosthesis. First, the condylar surface is prepared to receive the prosthesis, including resection of the entire condylar surface and drilling of femoral peg holes. The guide portion 6 of the rotary mill 2 is then fixed on the femoral condyle by inserting the attachment pegs 28, 30 into the pre drilled femoral peg holes. The guide portion 6 can be seen in position on the femoral condyle in FIG. 4. The body portion 4 is then seated on the guide portion 4, the guide peg 24 being receiving within the bore 20 of the rotary body 8. The shank 16 of the body portion is then attached to a surgical drill and the body portion 4 is guided to mill the bone superior to the anterior edge of the condylar plate 46 of the guide portion. Milling takes place with the leg flexed, so that the milling surface 10 does not contact the tibia. Referring to FIG. 4, it can be seen that if the leg is not sufficiently flexed, the milling surface 10 can clip the tibial surface as the rotary body advances along the dotted line DL.

The guide peg 24 guides the orientation of the body portion 4, ensuring that the milling surface 10 removes the bone tissue from the correct part of the femur. The body portion 4 advances along the guide peg 24 as bone tissue is removed. As the body portion 4 advances, the nodules 27, 29 act as stop pegs, upper surfaces of the nodules 27, 29 abutting the stop surface 15 that extends radially inwardly from the annular milling surface 10 and preventing further movement of the body portion 4, thus limiting the amount of bone that is removed.

Figure 5:
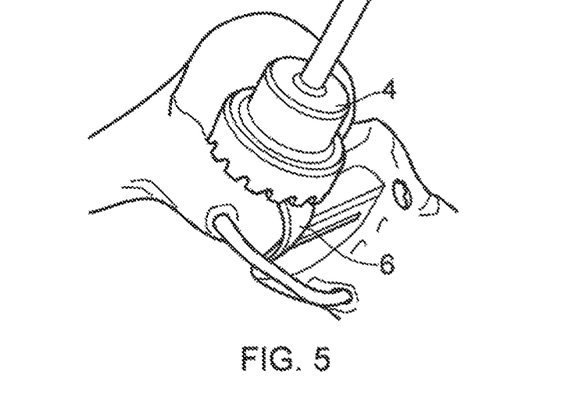
FIG. 5 shows a rotary mill in position on a femur.

The body portion 4 is dimensioned so as to ream only the anterior bone superior to the guide portion. As can be seen from FIGS. 5 and 6, provided that the leg is sufficiently flexed, the milling surface 10 does not disturb the adjacent soft tissues and so causes minimal damage or disruption to the surrounding structures, removing only that bone which is desired to be removed. As illustrated particularly in FIG. 5, the guide peg 24 is angled such that, when fully seated on the guide peg 24, the body portion 4 has only reamed the bone superior to the anterior edge of the guide portion 6. The reamed area of bone can be seen at area 38 on FIG. 6.

Additional tools can then be attached to the guide portion if necessary. For example, a posterior osteophyte guide 40 can be attached posteriorly to the guide portion 6. The osteophyte guide is a slotted tool that may be used to guide a chisel to remove osteophytes from the posterior area of the femoral condyle, helping to prevent femoral loosening.

Figure 7:
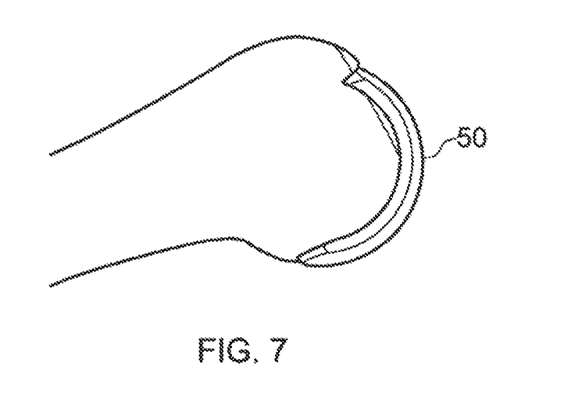
FIGS. 7 and 8 illustrate prosthesis components in position on a femur, with and without bone removal.
Figure 8:
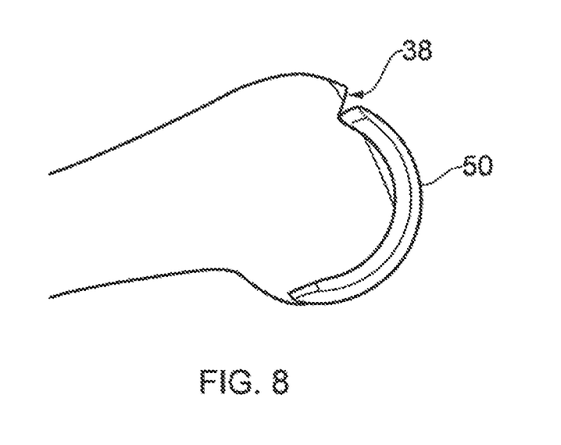
Figure 9:
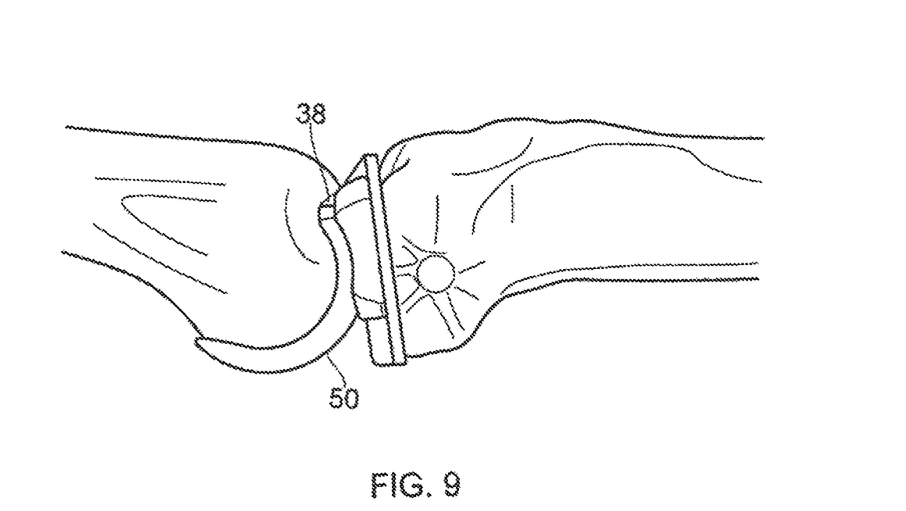
FIG. 9 illustrates an implanted unicondylar prosthesis.

Once all necessary bone removal has been completed, the guide portion 6 of the rotary mill 2 is removed and the appropriate prosthesis component is implanted, FIGS. 7 and 8 illustrate the area 38 of bone that is removed by the rotary mill 2. On FIG. 8, this area 38 can be seen immediately superior to the femoral prosthesis component 50. On FIG. 7, the rotary mill 2 has not been used and bone tissue remains superior to the prosthesis component 50. This bone tissue will cause impingement of the maniacal component, as illustrated in FIG. 1. In contrast, and as illustrated in FIG. 9, when the mill has been used to remove bone over the desired area 38, no impingement of the meniscal component is seen, even with the knee in full extension.

It is envisaged that the guide peg 24 may be integral with the guide body 22 or may be detachable from, or adjustable relative to, the guide body 22, so as to allow limited adjustment of the angle of the guide peg 24 or of the height of the guide peg 24. Such adjustment allows a degree of flexibility to the surgeon in tailoring the rotary mill 2 to the precise needs of individual patients. For example, if it is desired to remove less than the usual amount of bone, the guide peg 24 may be caused to protrude further from the surface of the condylar plate 28. In this instance, the guide peg 24 also acts as a stop peg, the end surface 36 of the guide peg 24 contacting the base (not shown) of the bore 20 and preventing further movement. The guide peg may be caused to protrude to such an extent that it is engages as a stop peg before the stop surface 15 of the body portion 4 contacts the nodules 27, 29 of the guide body. It is also envisaged that the guide portion 6 of the rotary mill be provided as merely one of several available guide portions, each being of a different size to accommodate different sizes of knee. Thus, each size of prosthesis may have an associated guide portion 6 of the appropriate size. Each guide portion 6 will have a suitable guide peg, of a height and at an angle that is determined to be most appropriate for the associated prosthesis.

It will be appreciated that the guide portion 6 may be employed together with other embodiments of body portion 4, including a range of rotary cutting devices. One embodiment of rotary cutting tool with which the guide portion 6 may be employed is illustrated in FIGS. 10 and 11. The rotary cutting tool 100 comprises a rotary body 102 and a guide shaft 104. The guide shaft 104 is at least partially received within a blind axial bore 106 formed within the rotary body 102. A closed proximal end (towards the left in the Figures) of the rotary body 102 terminates in a drive shaft 108, operable to be received within the chuck of a surgical drill (not shown). An open distal end of the rotary body 102 flares outwards to terminate in an annular receiving plate 110 extending about the opening of the axial bore 106 and described in further detail below.

The guide shaft 104 comprises an inner portion 112 and an outer portion 114. The inner portion 112 composes a solid shaft a distal end 116 of which is telescopically received within a proximal end 118 of the outer portion 114. The outer portion 114 comprises a substantially hollow shaft. A biasing spring 120 is mounted about the inner portion 112 of the guide shaft 104. The spring 120 rests at one end on the annular end surface 122 of the proximal end 118 of the outer portion 114. The other end of the spring 120 engages on an end cap 124 formed on a proximal end 126 of the inner portion 112. In an alternative embodiment (not shown) the spring 120 may engage on the blind end 128 of the axial bore 106 in which the guide shalt 104 is received.

The guide shaft is received freely within the bore 116 of the rotary body 102. An annular shoulder 130 is formed or the inner surface of the bore 106, dividing the bore into a distal section and a proximal section, the distal section being of larger inside diameter than the proximal section. A corresponding annular shoulder 132 is formed on the outer surface of the outer portion 114 of the guide shaft, dividing the outer portion into proximal and distal sections, the distal section being of larger outside diameter than the proximal section. The corresponding annular shoulders 130, 132 function as a depth stop, preventing the outer portion 114 of the guide shaft 104 from being received into the rotary body 102 beyond a certain point. This position is illustrated in FIG. 11. The larger diameter distal section of the outer portion 114 of the guide shaft may also serve to centre the guide shaft within the bore 106 of the rotary body 102.

Referring particularly to FIG. 10, the annular receiving plate 110 comprises a series of formations, operable to releasably engage an am annular cutting plate (not shown). The formations comprise at least one screw head 134 and a plurality of magnets 136, the magnets being recessed into the annular receiving plate so as to present a smooth surface. The annular cutting plate (not shown) comprises an annular cutting surface, similar to that described above with reference to the body portion 6, end an opposed annular engaging surface. The annular engaging surface comprises corresponding recesses and magnetic elements enabling the cutting plate to be releasably yet securely attached to the receiving plate 110 of the rotary body.

In use, the rotary cutting tool 100 is first assembled and then placed over the guide peg 24 of the guide portion 6. The guide peg 24 is received within the hollow outer portion 114 of the guide shaft until a distal end 138 of the outer portion 114 is seated against the surface 34 from which the guide peg 24 protrudes. The rotary body 102 is then connected to a surgical drill (not shown) via the drive shaft 108 and the rotary tool is guided to mill away the desired area of bone. During the cutting operation, the outer portion 114 of the guide shaft 104 remains seated in position over the guide peg 24. Downward pressure applied to the rotary body engages the blind end 138 of the bore 106 against the end cap of the inner portion 112 of the guide shaft 104, causing the inner portion 112 to be pushed further into the outer portion 114. This action compresses the spring 120 acting between the inner and outer portions. In this manner, the spring 120 damps the downward motion of the rotary body, assisting the control of the surgeon and thus increasing the ease with which the tool may be employed. The inner portion 112 of the guide shaft 104 continues to slide further into the outer portion 114 until the annular shoulder 130 on the rotary body 102 engages the annular shoulder 132 on the outer portion 114 of the guide shaft At this point the rotary body cannot travel any further towards the bone and the drilling action ceases.

FIG. 1 shows how the guard projection 7 functions to protect the proximal tibial surface 11 during milling of the femur 13. The guard projection can take many forms and may be a separate component attached to the guide body 6. In the illustrated embodiment, the guard projection 7 is integrally faced with the guide body 6 and may for example be cast or machined as a single component with the guide body 6. The guard projection 7 projects from the guide body 6 substantially parallel to the guide peg 24 and its free end 15 is spaced from the guide peg 24 by a distance slightly larger than the radius of the an milling surface 10, so that as the rotary body 8 travels along the guide peg 24, following the dotted line DL of FIG. 12, the rotary body just clears the guide projection 7 without impingement.

A semi-circular recess 17 may be formed in the guard projection 7 to provide clearance for the rotary body 5 as it proceeds along the dotted line DL of FIG. 12.

A distal surface of the guard projection 7 is provided with a tibial contact surface 19 which may be polished and have chamfered edges to prevent damage to the tibia in use.

It will be appreciated that with the guard projection 7 attached to the guide portion 6, the guide portion 6 cannot be fitted to the femur unless the leg of the patient is sufficiently flexed. Thus, the guide projection 7 serves to assist the surgeon in achieving the required leg alignment, such that the tibial contact surface 19 sits substantially flat against the resected proximal end of the tibia. With this alignment the guard projection 7 closes off the gap between the annular milling surface 8 and the tibia and prevents soft tissue getting into this gap during milling of the femur.

For the full travel of the of the rotary body 8 relative to the guide body 22, the guard projection 7 closely receives the annular milling surface 10 of the rotary body 8 and prevents the milling teeth 12 of the milling surface 10 from coming into contact with the tibia, whatever the degree of flexion of the leg.

The invention claimed is:

1. A rotary mill comprising a body portion having a milling surface for milling a first bone, a guide portion having a guide body, and inter-engageable guide formations formed on the body portion and guide portion, the guide body having a projection which is adapted to hold a second bone away from the rotary mill during the milling operation, wherein the inter-engageable guide formations comprise a central bore extending along a rotary axis of the body portion and a guide peg extending from the guide body, the guide peg being operable to be received in the central bore of the body portion.

2. The rotary mill as claimed in claim 1, wherein the projection is integrally formed with the guide body.

3. The rotary mill as claimed in claim 1, wherein the projection comprises an arm which is shaped to receive the milling surface without impingement.

4. The rotary mill as claimed in claim 1, wherein the projection is shaped to receive the milling surface closely over its full range of movement relative to the guide body.

5. The rotary mill as claimed in claim 1, wherein the projection is provided with a recess on a first side which is adapted to a.ccommodate the milling surface without impingement.

6. The rotary mill as claimed in claim 1, wherein a second side of the projection may be polished chamfered or otherwise shaped to avoid damage to the second bone.

7. The rotary mill as claimed in claim 1, wherein the projection is removeably attached to the guide body.

8. The rotary mill as claimed in claim 1, wherein the projection extends from the guide body in a direction substantially parallel to a longitudinal axis of the guide peg.

9. The rotary mill as claimed in claim 1, further comprising additional guide portions, each guide portion being of a different size to other guide portions.

10. The rotary mill as claimed in claim 1, wherein the guide peg comprises an abutment surface operable to abut a corresponding abutment surface in the central bore of the body portion.

11. The rotary mill as claimed in claim 10, wherein the abutment surface comprises a distal surface of the peg.

12. The rotary mill as claimed in claim 11, wherein the guide body has substantially the form of a trial prosthesis component.

13. The rotary mill as claimed in claim 1, wherein the guide body comprises a trail prosthesis component.

14. The rotary mill as claimed in claim 13, wherein the guide body comprises a trial unicondylar femoral prosthesis component.

15. The rotary mill as claimed in claim 14, wherein the guide body is operable to guide reaming of a region superior to the anterior edge of the guide body.

16. The rotary mill as claimed in claim 1, wherein the inter-engageable guide formations comprise a central bore extending along a rotary axis of the body portion and a guide peg extending from the guide body, the guide peg being operable to be received in the central bore of the body portion, and wherein the projection is integrally formed with the guide body.

17. A rotary mill comprising a body portion including a first guide formation and a mulling surface adapted for milling a first bone; and a guide portion including a second guide formation and a projection adapted to hold a second bone away from the rotary mill while milling the first bone; the first guide formation structured to mate with the second guide formation to slidably couple the body portion to the guide portion, wherein the first guide formation comprises a bore and the second guide formation comprises a peg configured for insertion within the bore.

18. The rotary mill of claim 17, wherein the projection includes a polished bone contacting surface configured to sit substantially flat against a resected end of the second bone.

* * * * *

UNITED STATES PATENT AND TRADEMARK OFFICE
CERTIFICATE OF CORRECTION

PATENT NO.       : 11,304,707 B2
APPLICATION NO.  : 16/533427
DATED            : April 19, 2022
INVENTOR(S)      : Ridley et al.

Page 1 of 1

It is certified that error appears in the above-identified patent and that said Letters Patent is hereby corrected as shown below:

On the Title Page

Item (71), Column 1, Line 3, delete "Murray;" and insert --Murray, Oxford (GB);-- therefor Item (71), Column 1, Line 3, delete "Dodd;" and insert --Dodd, Oxford (GB);-- therefor Item (71), Column 1, Line 4, delete "O'Connor" and insert --O'Connor, Oxford (GB)-- therefor Page 2, Column 2, under item (56) "Other Publications", Line 36, delete "Aciton" and insert --Action-- therefor In the Claims In Column 7, Line 31, in Claim 5, delete "a.ccommodate" and insert --accommodate-- therefor Signed and Sealed this
Twenty-fifth Day of October, 2022

*Katherine Kelly Vidal*

Katherine Kelly Vidal
*Director of the United States Patent and Trademark Office*